United States Patent
Schulz et al.

(10) Patent No.: US 7,995,206 B2
(45) Date of Patent: Aug. 9, 2011

(54) APPARATUS AND METHOD FOR RECOGNIZING OBJECTS

(75) Inventors: Rüdiger Schulz, Kleinmachnow (DE); Erik Sommer, Schöneiche (DE); Michael Schmidt, Neukirchen (DE); Marko Wohlfahrt, Glauchau (DE); Jan Richtsteiger, München (DE); Thomas Bartsch, Lichtenstein (DE); Falk Schneider, Dresden (DE)

(73) Assignees: BITS Zwickau Büromat IT-Systeme GmbH, Zwickau (DE); PETROTEST Instruments GmbH & Co. KG, Dahlewitz (DE)

( * ) Notice: Subject to any disclaimer, the term of this patent is extended or adjusted under 35 U.S.C. 154(b) by 207 days.

(21) Appl. No.: 12/300,473

(22) PCT Filed: May 10, 2007

(86) PCT No.: PCT/EP2007/004166
§ 371 (c)(1),
(2), (4) Date: Mar. 6, 2009

(87) PCT Pub. No.: WO2007/131708
PCT Pub. Date: Nov. 22, 2007

(65) Prior Publication Data
US 2009/0201508 A1   Aug. 13, 2009

(30) Foreign Application Priority Data

May 12, 2006 (DE) .......................... 10 2006 022 717

(51) Int. Cl.
*G01N 21/55* (2006.01)
*G01N 21/47* (2006.01)

(52) U.S. Cl. .......................................... 356/445; 356/446
(58) Field of Classification Search .......... 356/445–448, 356/450–458
See application file for complete search history.

(56) References Cited

U.S. PATENT DOCUMENTS

| | | | | |
|---|---|---|---|---|
| 3,506,928 A | * | 4/1970 | Adrianus | 372/24 |
| 3,809,891 A | | 5/1974 | Erdman et al. | |
| 5,106,196 A | * | 4/1992 | Brierley | 356/445 |
| 5,917,594 A | * | 6/1999 | Norton | 356/327 |
| 6,128,093 A | * | 10/2000 | Niikura | 356/432 |

FOREIGN PATENT DOCUMENTS

| | | |
|---|---|---|
| DE | 213061 A1 | 8/1984 |
| JP | 61272680 A | 12/1986 |
| JP | 2000338262 A | 12/2000 |

* cited by examiner

*Primary Examiner* — Gregory J Toatley
*Assistant Examiner* — Jarreas C Underwood
(74) *Attorney, Agent, or Firm* — Laurence A. Greenberg; Werner H. Stemer; Ralph E. Locher

(57) ABSTRACT

An apparatus for recognizing objects with a laser light source and a light receiver has an at least partly reflective wall and an interspace between the laser light source and the wall, through which an object can be moved or in which an object can be placed. A movable mirror device is arranged between the laser light source and the wall in such a way that light emitted by the laser light source can be directed onto the wall. In a method for recognizing objects a mirror device directs the light onto an at least partly reflective wall and is controlled in such a way that the wall is irradiated by the light. The light receiver detects the light reflected from the wall and, in the process, registers an object moving or placed between the laser light source and the wall by way of a change in the reflected light detected.

19 Claims, 6 Drawing Sheets

APPARATUS AND METHOD FOR RECOGNIZING OBJECTS

BACKGROUND OF THE INVENTION

Field of the Invention

The present invention relates to an apparatus and a method for recognizing objects with a light source and a light receiver.

An apparatus of this type is needed, for example, in order to determine the softening point of a bitumen or bitumen-containing binder to be tested in the ring and ball method described in the European Standard EN 1427. In this case, in a transparent vessel filled with a liquid, steel balls lying on platelets of a bitumen layer on a ring holder are provided and, during the controlled heating of the liquid in the course of the test, fall downward, encased in softened bitumen material, and are detected at a distance of 25.0±0.4 mm underneath the ring holder. In order to be able to detect the balls falling down at the measurement point, use is made of a light barrier comprising an LED and a light receiver, for example, arranged at the edge of the vessel. This principle has the disadvantage that disturbances in the liquid, such as bubbles rising in the vessel as a result of the heating or viscosity-dependent stratification in diverse test media, can be misinterpreted by the light barrier as the ball and thus can lead to unreliable results.

BRIEF SUMMARY OF THE INVENTION

The object of the present invention is therefore to provide an apparatus and a corresponding method for recognizing objects, such as the above-described falling balls, which are reliable and nevertheless can be applied easily.

This object is achieved by an apparatus for recognizing objects with a light source and a light receiver in which the light source is a laser light source, the apparatus has an at least partly reflective wall and, between the laser light source and the wall, an interspace is provided, through which an object can be moved or in which an object can be placed, and a movable mirror device is arranged in the beam path between the laser light source and the wall in such a way that light emitted by the laser light source can be directed onto the wall, wherein the movement of the mirror device can be controlled in such a way that the wall can be irradiated with the light emitted by the laser light source, at least along a line, and light reflected from the wall can be detected by the light receiver.

By using the apparatus according to the invention, it is possible to use a change in the intensity of the light radiation reflected from the wall as an indicator for recognizing an object present between the laser light source and the wall. Since the light beam emerging from the laser light source can scan an entire line on the wall, given an appropriate scanning frequency and resolution of the reflected light radiation detected by the light receiver, not only the object itself but also its position on the projection line of the laser light source, determined during the measurement, and also the size of the object can be registered. It is thus possible for reliable recognition of moving and also stationary objects to be ensured with a relatively simple arrangement.

It is quite particularly advantageous if the wall has alternating light and dark regions. With the aid of the light and dark regions on the wall, markings can be set, by using which accurate determination of the size and position of the object is possible. For instance, if an opaque object moves past the light and dark regions of the wall or is placed in front of this region, these are covered, at least briefly, so that at this time the light receiver is not able to pick up reflected light radiation, in particular from the light regions, or can pick up light radiation reduced by the disturbance. If, for example, a light region is registered by the light receiver as a high level and a dark region as a low level, when an object is moved past or placed on a light region, a signal change occurs in the light receiver in which, instead of a high level for the corresponding light regions of the wall, a low level is registered. In this way, the position of the object can be defined by using the position of the light regions covered by the object, it being possible to draw conclusions about the size of the object from the number of light regions covered.

It has been proven to be particularly beneficial if the light and dark regions of the wall form a regular stripe pattern. Such a stripe or bar pattern can be registered in the light receiver as a regular 0-1 bit pattern, for example. If an object moves past the stripe pattern or is placed in front of the stripe pattern, a disturbance occurs in the bit pattern, which manifests itself for example by a change from high levels to low levels. In this case, the density and the width of the stripes can be matched to the size of the objects to be recognized, so that the most accurate possible identification of the respective object size is possible.

According to a further advantageous variant of the invention, the light emitted by the laser light source is pulsed. In this arrangement, laser pulses with specific frequencies can be used in order to scan a line on the wall, wherein the frequency of the laser pulses used can be employed to resolve the objects moving or placed between the laser light source and the wall. Thus, in the case of this arrangement for the object recognition, it is not absolutely necessary for the wall to have light and dark regions.

According to a beneficial example of the invention, the mirror device has an electronically controllable oscillating mirror. For example, rotating faceted mirrors or else swinging mirrors can be used. As a result of the movability of such a mirror, laser beams in the form of a dot can simply be projected as a line onto a measurement field on the wall. During a measurement, the speed of movement of the mirror device is preferably set as a constant value.

According to an advantageous embodiment of the invention, the light receiver has a light sensor which is coupled to an evaluation unit. The evaluation unit can for example convert values determined by the light sensor into high levels for light regions and low levels for dark regions, which data can be compared with a reference pattern in order to recognize an object moved or placed between the laser light source and the wall.

The evaluation unit preferably has a contrast control unit. By using this, it is possible to set the intensity of the light radiation received by the light receiver which is to be classified as a light region or as a dark region. For instance, it is possible that a reflective region of the wall only reflects light diffusely through an object appearing in front of it, so that although reflected light radiation from this region is received by the light receiver, the received signal has a low intensity. In such cases, with the aid of the contrast control unit, the contrast can be set in such a way that signals with an attenuated intensity are classified as low levels.

According to a preferred design variant of the present invention, the laser light source and the light receiver are combined in a scanning module having an uncoded high-low output signal. Thus, the laser light source and the light receiver can be accommodated in a practical manner in one instrument, which simplifies the measuring apparatus for a user. In addition, in this way the alignment of the laser light source and the light receiver with each other can be coordinated accurately and fixedly. The uncoded output signal additionally makes it possible to detect objects in the area of registration of the scanning module in a straightforward manner.

The apparatus advantageously has a time and/or temperature registering unit. Thus, the time and/or the temperature during which the object was registered by the apparatus according to the invention can be determined, wherein the object recognition can be combined logically with the time and/or temperature recognition.

In a specific configuration of the present invention, the moved object is a ball, which is arranged in a liquid provided in a transparent vessel such that it can fall downward, the laser light source, the light receiver, the mirror device and the wall being arranged around the vessel. Such an arrangement can be used to draw conclusions as to the time at which the fall of the ball had started by using the time at which the ball is registered. Likewise, this apparatus can be used to determine a speed of movement of a ball in a liquid.

According to a particularly preferred embodiment of the invention, the ball is held on a softenable layer in a ring holder, below which a measurement region for registering the ball is provided at a distance of 25.0±0.4 mm. This arrangement is used in particular for the use of the apparatus in what is known as the ring and ball method, in which the softening point of bitumen or bitumen-containing binder layers is determined. For instance, an arrangement which is described in the European Standard EN 1427:1999 could be used.

The object of the invention is further achieved by a method for recognizing moving objects with a light source and a light receiver in which the light source is a laser light source, from which light is directed onto a movable mirror device, wherein the mirror device directs the light onto an at least partly reflective wall and the mirror device is controlled in such a way that the wall is irradiated by the light, at least along a line, and wherein the light receiver detects the light reflected from the wall and, in the process, registers an object moving or placed between the laser light source and the wall by means of a change in the reflected light detected.

With the method according to the invention, objects between the laser light source and the wall can be recognized along the entire line registered by the laser light, it being possible for the light source and the light receiver to be arranged on the same side of the apparatus, opposite the wall, which makes it possible to integrate the light source and the light receiver in a scanning module. With the aid of this method, objects can thus be registered reliably in a straightforward manner.

According to a preferred embodiment of the invention, the light receiver is coupled with an evaluation unit, which outputs a high level for light regions of the wall and a low level for dark regions of the wall in an output signal. Thus, it is possible to use light and dark regions of the wall in order to recognize objects moved past the wall or placed there by using the intensity changes of the reflected laser light received by the light receiver.

In this case, it is particularly beneficial if a regular stripe pattern provided on the wall is registered by the light receiver with the evaluation unit as a continuous, uncoded 0-1 bit pattern. In this case, the uncoded 0-1 bit pattern without a disturbing object located between the light source and the wall forms a suitable reference pattern which makes it possible, when it is disturbed by an object, not only to register the object itself but also its size.

It is particularly advantageous if the output signal is disturbed by the object in such a way that, in the region in which the object is moved or placed, low levels are registered instead of high levels. By this means, in a straightforward but unambiguous way, an accurate statement is possible as to whether there is an object between the light source and the wall or not.

According to a further, likewise very advantageous, embodiment of the invention, the light from the laser light source is radiated onto the mirror device in pulsed form. Therefore, the laser light can be projected onto the wall by the mirror device in pulsed form, and the light reflected from the wall can be registered by the light receiver in corresponding pulses, wherein, by using the frequency used, it is possible to determine accurately at what time and at what point the object was detected between the laser light source and the wall.

In a specific example of the invention, a ball falling in a liquid in a transparent vessel is registered. With this method, by using the time of registration of the ball, it is possible to draw conclusions about the time of the start of its fall in the vessel. It is also possible with this method to determine the speed of movement of the ball in the liquid.

According to a particularly preferred example of the invention, the ball is a steel ball which, before falling, rests on a layer in a ring arrangement, the layer being softened at a specific temperature and the ball encased by the layer material falling downward, the ball being registered after a specific fall travel. This method is particularly highly suitable for use in what is known as the ring and ball method for determining the softening point of bitumen or bitumen-containing binders, which, for example, is described in the European Standard EN 1427:1999, to which reference is made here.

Characteristics, the mode of action and advantages of the present invention will be described in the following text by using the figures of the drawing, in which

BRIEF DESCRIPTION OF THE SEVERAL VIEWS OF THE DRAWING

FIG. 5 shows a bit pattern without disturbing object according to the stripe pattern from FIG. 4;

FIG. 7 shows a bit pattern with disturbing object according to the stripe pattern from FIG. 6;

DESCRIPTION OF THE INVENTION

Figure 1:
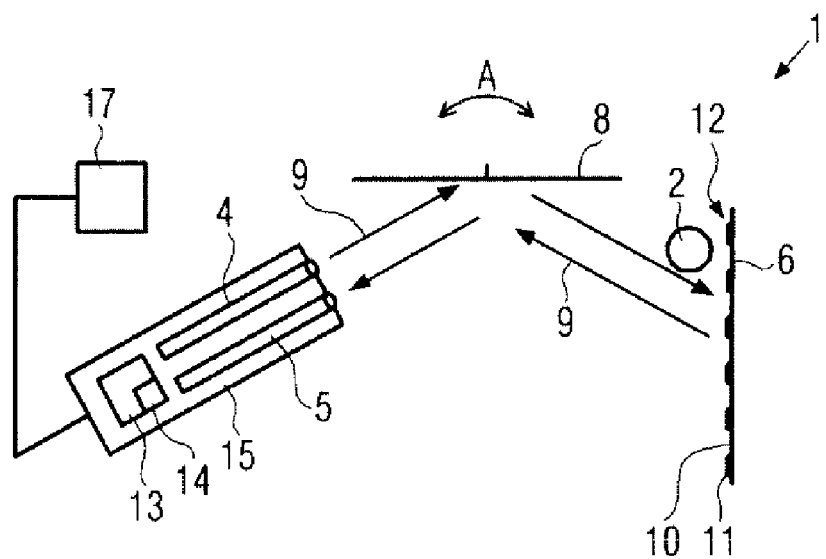
FIG. 1 shows schematically the functional principle of a first embodiment of the present invention.

FIG. 1 shows schematically the functional principle of an apparatus 1 according to the invention for recognizing an object 2 moved between a laser light source 4 and a wall 6.

In the apparatus 1, the laser light source 4 and a light receiver 5 are arranged opposite the wall 6, light 9 which is emitted by the laser light source 4 first being directed onto a mirror device 8 and being projected by the mirror device 8 onto the wall 6. For this purpose, the laser light source 4 is arranged at an angle to the reflective surface of the mirror device 8.

The mirror device 8 comprises a movable, electronically controllable oscillating mirror, which can be pivoted in accordance with the directions of movement indicated by the arrow A. The mirror device 8 is coupled with an electronic control module, which is not illustrated in FIG. 1. The mirror device 8 can, for example, be a rotating faceted mirror or else a swinging mirror.

As a result of its movement, the mirror device 8 projects a point-like laser beam 9 emitted by the laser light source 4 as a line onto a measuring area on the wall 6.

Figure 2:
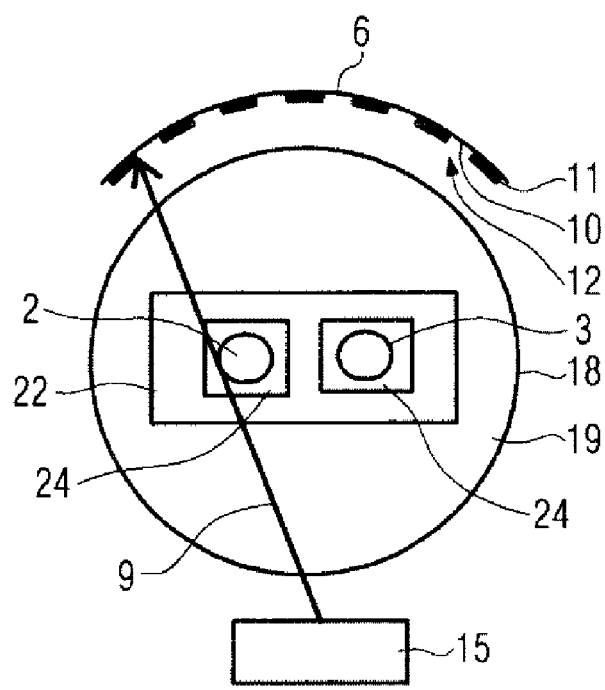
FIG. 2 shows schematically the functional principle of the apparatus from FIG. 1 by using a ring-ball measuring arrangement in plan view.

In FIG. 1, the wall 6 is illustrated as a flat surface but, in other embodiments of the invention, as shown in FIG. 2, can also be formed as a curved surface. The surface of the wall 6 that faces the laser light source 4 is at least partly reflective. In the example shown in FIG. 1, the wall 6 has on the side facing the laser light source light regions 10 and dark regions 11, which form a regular stripe pattern 12 in the example shown.

Arranged opposite the wall 6 is a light receiver 5 for the light 9 reflected from the wall 6. The light receiver 5 has the same orientation as the laser light source 4, so that it is able to receive via the mirror device 8 light 9 which is reflected from the wall 6 and which falls onto the mirror device 8. The light receiver 5 is combined with the laser light source 4 in a scanning module 15.

The light receiver 5 has a light sensor which is coupled with an evaluation unit 13 for the light signals received. Provided in the evaluation unit 13 is a contrast control unit 14 having a threshold switch for setting the contrast of the light 9 received.

In addition, the apparatus 1 has a time and temperature registering unit 17, which is coupled with the evaluation unit 13. In other embodiments of the invention, not shown, time and temperature can also be registered with mutually independent measuring devices for registering the time or the temperature.

If laser light 9 from the laser light source 4 is radiated onto the mirror device 8, the mirror device 8 projects the laser beam 9 in a line onto the wall 6 as a result of its movement, the line of light produced in the process intersecting the stripes 12 provided on the wall 6 approximately at right angles. By means of the regular stripe pattern 12, light beams 9 are reflected or not reflected or diffusely reflected at regular intervals by the wall 6. In this way, the light sensor of the light receiver 5 receives light signals with higher intensity and light signals with lower intensity or, for specific regions, even no light signals.

By means of the evaluation unit 13, the light signals of higher intensity are picked up as high level and light signals with lower intensity are picked up as low signals and combined in a high-low output signal 16. The high-low output signal 16 can be registered as a 0-1 bit pattern 23. An undisturbed 0-1 bit pattern 23 can be used as a reference pattern for a comparison with a bit pattern with a disturbing object 2.

The contrast control unit 14 provided in the evaluation unit 13 is able to set the contrast of the light registered by the light sensor in such a way that those signals which lie above a specific threshold value are classified as high signals, and the signals which lie below this threshold value are classified as low signals. For this purpose, the contrast control unit 14 has a threshold value switch with which adaptation to the contrast relationships between the reference background on the wall 6 and an object 2 moved or placed in front of the latter can be carried out.

If an object 2 moves in an interspace 7 between the laser light source 4 and the wall 6, past the line projected onto the wall 6 by the mirror device 8, or if said object is placed there, the light signals registered by the light receiver 5 will be changed, at least for a short time. By means of the object 2, irregularities are produced in the bit pattern 23 generated by the evaluation unit 13, since the object 2, at least if it has opaque regions, prevents or reduces reflection of the light regions 10 of the wall 6, so that the intensity of the light beams reflected from the light regions 10 of the wall 6 is reduced by the object 2. In a corresponding way, at the point at which the object 2 has moved past the wall 6 or at which it is located, instead of high levels which correspond to the light regions 10 of the wall 6, low levels are registered by the light receiver 5, at least for a short time.

If the stripe pattern 12 on the wall 6 is sufficiently dense and if the stripes and the spaces between them are correspondingly narrow, a plurality of light regions 10 can be covered by the object 2 so that, at the point at which the object 2 has moved past the wall 6 or at which it is placed, a series of low levels or 0 values in the 0-1 bit pattern 23 is determined. From the number of low levels or the 0 values, it is possible to derive how large the object 2 is. In addition, the position of the object 2 can be concluded from the position of the bit pattern disturbance determined.

The apparatus described above and the method can be used to register moving and stationary objects between the laser light source 4 and the wall 6.

Figure 3:
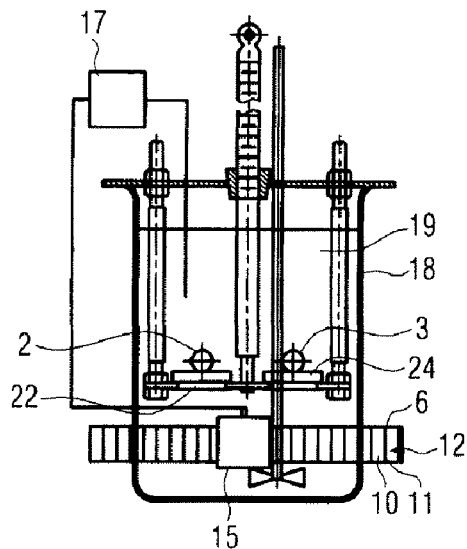
FIG. 3 shows schematically the arrangement from FIG. 2 in side view.

FIG. 2 shows schematically in plan view the functional principle of the apparatus 1 according to the invention described by using FIG. 1, by using a specific design variant of the invention, and FIG. 3 shows this embodiment in side view.

In the embodiment of the invention shown in FIGS. 2 and 3, two objects 2, 3 to be measured are located in a transparent beaker 18, which is filled with a transparent liquid 19. The objects 2, 3 to be measured are two steel balls here, which each rest on layers consisting of bitumen platelets 24, which are held in a ring holder 22.

Provided around the beaker 18, on one side of the vessel 18 and underneath the ring holder, is a curved wall 6, on which a vertical stripe pattern 12 is depicted.

Opposite the wall 6, on the other side of the beaker 18, there is a scanning module 15 having a laser light source 4, a mirror device 8 and a light receiver 5. By means of the mirror device 8 provided in the scanning module 18, a laser beam 9 emerging from the laser light source 4 is projected onto the wall 6 in such a way that the result is a laser light line intersecting the stripe pattern 12 on the wall 6.

The laser light reflected from the light regions 10 of the wall is received by the light receiver 5 by means of the mirror device 8 in the scanning module 15. In this case, initially, which means without an object located between the scanning module 15 and the wall 6, a regular 0-1 bit pattern 23 is formed in the evaluation unit 13 of the scanning module 15, corresponding to the regular stripes of the stripe pattern 12 on the wall 6.

At the start of the measurement, by using a time and/or temperature registering unit 17, the start of the measurement is defined as t=0. The liquid 19 is then heated continuously while stirring the liquid 19 continually and the temperature is measured until the bitumen platelets 24 on which the balls 2, 3 rest soften, whereupon the balls 2, 3, encased by the bitumen material 24, fall through the ring holder 22.

Once the balls 2, 3 reach the measuring region, which is located 25±0.4 mm below the ring holder 22, the balls 2, 3 are registered by the scanning module 15, the time and temperature registering unit 17 registering the associated time h or $t_3$ and the corresponding temperatures $T_2$ and $T_3$.

At the times at which the balls 2, 3 fall in front of the stripe pattern 12 of the wall 6, in each case light regions 10 of the stripe pattern 12 are covered, so that the light receiver 5 in the scanning module 15 receives a low signal from these regions. From the number of low signals, the evaluation unit 13 in the scanning module 15 determines the size of the object that has fallen and can then establish whether it is actually one of the balls 2, 3 or whether, for example, the size of the object determined points rather more to the fact that the object recognized is a bubble rising in the vessel 18.

The evaluation unit 13 has software which, depending on the frequency of the laser light source 4 used, the type of laser light source 4, the distance of the scanning module 15 and of the wall 6 from the vessel 18, the composition of the liquid 19, the refractive index of the wall of the vessel 18 and/or further constructional or test-specific features, processes the data acquired.

The scanning module 15 used in the apparatus of FIGS. 2 and 3 is a non-decoded scanning engine. This means that the scanning module 15 supplies only a digitized signal from its scanning logic but does not convert the pattern read into a specific barcode set. The evaluation unit 13 of the scanning module 15 uses two digital signals, via which the time variation of a scanning cycle and the pattern read can be determined, examples of such signals being illustrated in FIGS. 8 and 9. In the embodiment shown in FIGS. 2 and 3, it is important that the scanning module 15 has available as background on the wall 6 a pattern with sharp light and dark transitions, similar to those of a bar code, so that the functionality of the scanning module 15 is ensured.

Figure 4:
FIG. 4 shows schematically a stripe pattern without disturbing object.

FIG. 4 shows schematically an example of the stripe pattern 12 used in FIG. 3 without a disturbing object 2, 3. The stripe pattern 12 has alternating light and dark regions 10, 11, which are arranged at a regular distance from one another.

FIG. 5 shows a bit pattern 23 for the stripe pattern 12 from FIG. 4 without a disturbing object 2, 3. In a way corresponding to the regular stripe pattern 12, the result is a regular 0-1 bit pattern 23 without disturbances, which can be employed as a reference pattern.

Figure 6:
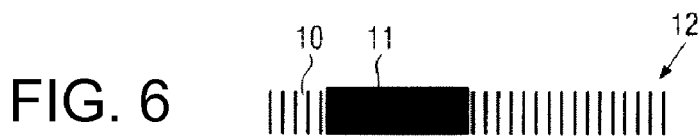
FIG. 6 shows schematically a stripe pattern with disturbing object.

FIG. 6 shows an example of a stripe pattern 12 with a disturbing object 2. At the point at which the object 2 has moved past the stripe pattern or at which it has been placed, no light regions 10 can be detected.

FIG. 7 shows a bit pattern 23 which corresponds to the stripe pattern 12 with disturbing object 2 from FIG. 6. At the point at which a disturbance by the object 2 took place, the bit pattern 23 has a series of 0 levels.

Figure 8:
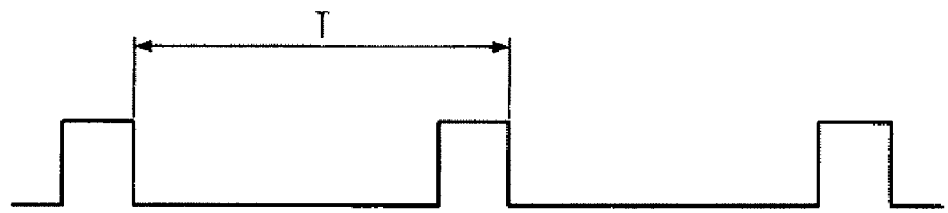
FIG. 8 shows an example of a signal from a scanning module, with which the time variation of the scanning operation is determined.

FIG. 8 shows an example of a signal from an evaluation unit 13, with which the time variation of the scanning operation can be determined. The signal shown in FIG. 8 in this case supplies a high-low edge at the start of the scan cycle, in the example illustrated here a measuring cycle having a period T of about 33 milliseconds to about 39 milliseconds. In this case, a scan cycle comprises a laser run from right to left and back again.

Figure 9:
FIG. 9 shows an example of an output signal having high and low levels from a scanning module.

FIG. 9 shows an example of an output signal 16 from an evaluation unit 13, the signal illustrated outputting a pattern read in. A low signal signals a dark, less reflective scanning region and a high signal should be assigned to a light, highly reflective region.

The background pattern depicted on the wall 6 preferably comprises black bars of a fixed width which have a constant spacing from one another. If there is no object 2, 3 between the scanning module 15 and the bar pattern 12, a regular high-low output signal 16 is to be recorded on a data out line of the scanning module 15. If an article or an object 2, 3 is introduced into the laser field of the scanning module 15, the bar pattern 12 will be interrupted, which leads to a change in the data out signal. Depending on the reflective properties of the object 2, 3, the signal at this point has either an extended low or high signal. This pattern interruption is then detected and evaluated with the aid of the a the evaluation electronics provided in the evaluation unit 13.

Figure 10:
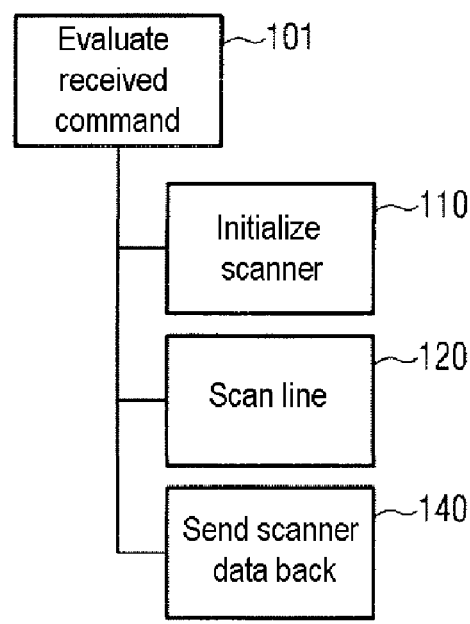
FIG. 10 shows a block diagram which illustrates the $I^2C$ handler function.

FIG. 10 shows schematically in a block diagram the steps to be coordinated by an $1^2C$ handler for the scanning module 15. In accordance with step 101, first of all a received command has to be evaluated. In step 110, the scanning module 15 is to be initialized. In step 120, a line on the wall 6 is scanned by the scanning module 15. In step 140, the scanning data is passed back to the evaluation unit 13. The scanned signals are read in by a PIC controller, the pattern read in is stored in suitable form and this is offered to a host controller via an $1^2C$ bus interface for further evaluation.

Figure 11:
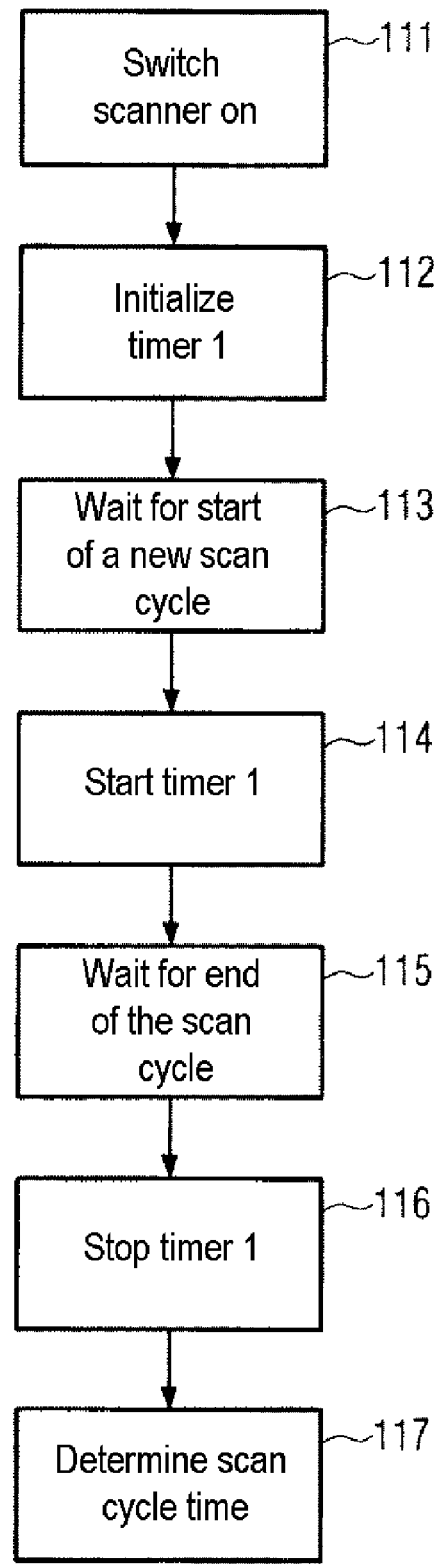
FIG. 11 shows the steps necessary to initialize the scanning module, by using a block diagram.

FIG. 11 shows schematically by using a block diagram how the scanner logic of the scanning module 15 is initiated with the aid of a specific 12C command. Here, in step 111 the scanning module 15 is first switched on and a wait is made for a specific settling time of the laser mechanism. In step 112, a timer "1" is initialized. In step 113, the start of a new scan cycle is awaited. In step 114, the timer "1" is started.

According to step 115, a wait is made for the end of the scan cycle. In step 116, the timer "1" is stopped and, in step 117, the scan cycle time is determined and stored in the PIC controller. After that, the scanning module 15 remains switched on.

Figure 12:
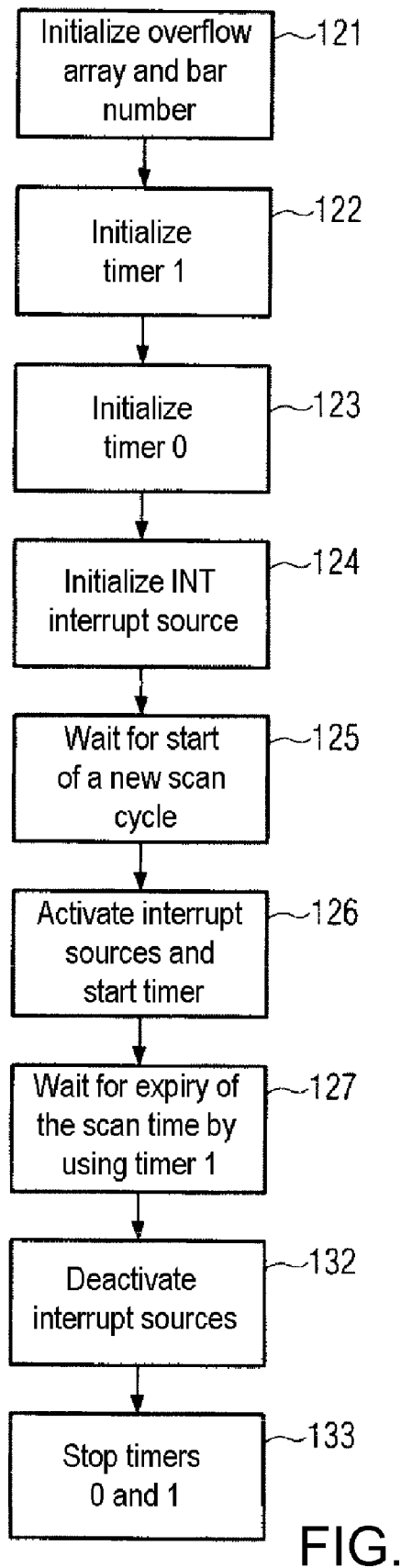
FIG. 12 shows the steps necessary to scan a line, by using a block diagram.

FIG. 12 shows schematically by using a block diagram the partial steps carried out in step 120 for the scanning of one line. If the host controller sends a command to read in a scan line to the PIC controller, then the latter begins with the pattern recognition routine. In step 121, an overflow array and a bar number are initialized. According to step 122, the timer "1" is initialized. In step 123, an internal timer, the timer "0", is initialized. Furthermore, in the pattern recognition routine, the data out signal of the scanning module 15 is used as an interrupt source (INT), which is initialized in step 124. In step 125, a wait is first made until a new scan cycle begins. Then, in step 126, the timer "0" and the interrupt source are activated. In addition, in step 127, the timer "1" is started, which supplies an interrupt after half the scan cycle time. When this interrupt occurs, then the reading has been completed, so that the data read in reproduces only the pattern for one direction of the laser, for example from right to left.

Figure 13:
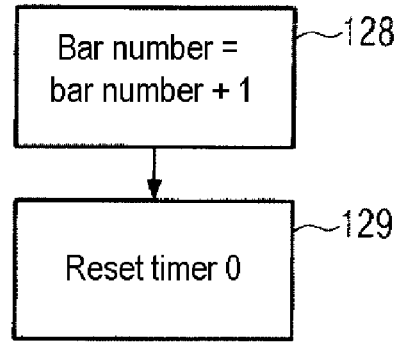
FIG. 13 shows the steps of an INT interrupt when recognizing a next bar, in a block diagram.
Figure 14:
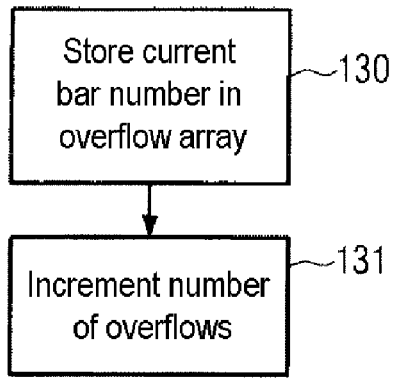
FIG. 14 shows the steps of a timer "0" overflow interrupt, in a block diagram.

The timer "0" is set in such a way that, after a specific time, which is much shorter than the total cycle time, it triggers an overflow interrupt. Before the start of the pattern recognition routine, a counter which contains a current bar number is then reset. When an INT interrupt occurs, which means a high-low edge of the data out signal, then the laser of the scanning module 15 is located on a new bar of the stripe pattern 12. As FIG. 13 shows, in step 128 the current bar number is incremented in the associated interrupt routine and in step 129 the timer "0" is reset. It is therefore possible to ensure that, given a regular bar pattern 12, the overflow interrupt from the timer "0" does not occur. However, if the stripe pattern 12 is interrupted, then the overflow occurs and a corresponding interrupt routine is executed, as shown in FIG. 14. Here, in step 130 the current bar number is stored in an overflow array and the number of overflows is incremented in step 131. If the overflow occurs repeatedly in one bar number, then the bar number is also stored repeatedly in the array.

Once the reading has been completed, the host controller is able to retrieve the data read in from the PIC controller and use it for further evaluation. In the process, it obtains the content of the overflow array, its size and the number of the last bar.

The stored bar numbers in the overflow array, in conjunction with the total number of bars, which is to say the number of the last bar, are then an indicator of the length and position of an interruption within the bar pattern 12. In this case, it does not matter whether the object 2, 3 which triggered the interruption led to an extended low or high signal 16 from the data out line. In step 132 of FIG. 12, the interrupt sources are deactivated and in step 133 the timers "0" and "1" are stopped.

Figure 15:
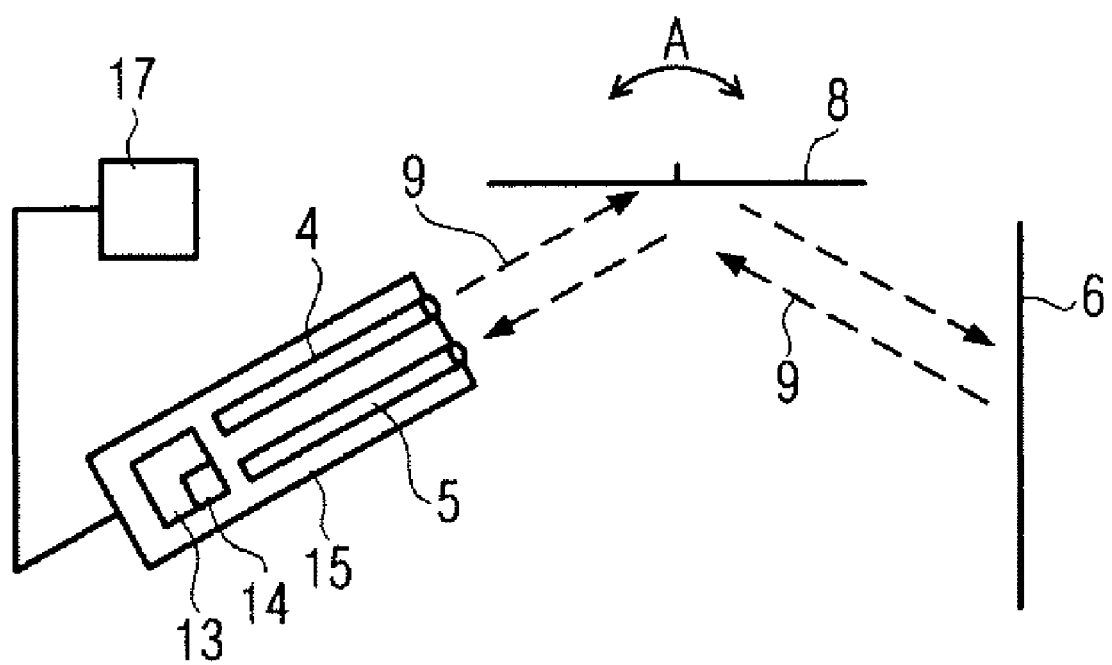
FIG. 15 shows schematically the functional principle of a further embodiment of the present invention.

FIG. 15 shows schematically a further possible design variant of the apparatus 1' according to the invention.

Since the apparatus 1' contains elements the same as or similar to the apparatus 1, the same designations for the same elements as in apparatus 1 are used below, reference being made to the description of these elements carried out above.

Like the apparatus 1, the apparatus 1' has a scanning module 15 arranged opposite an at least partly reflective wall 6 opposite, with a laser light source 4 and a light receiver 5 as well as an evaluation unit 13. Provided between the scanning module 15 and the wall 6 is a rotatable mirror device 8, with which laser light 9 can be projected onto the wall 6, laser light reflected from the wall 6 being received by the light receiver 5.

As distinct from the apparatus 1, the wall 6 of the apparatus 1' does not have a stripe pattern 12. The laser beams 9 emitted by the laser light source 4 are pulsed, however. If an object 2, 3 is moved between the laser light source 4 and the wall 6 or placed in the interspace 7 between the laser light source 4 and the wall, the intensity of the light received by the light receiver 5 changes. The point at which the object 2, 3 was detected can be determined in the apparatus 1' by using the frequency of the laser pulses employed. For example, a frequency of 10 kHz can be used for this purpose.

Also with the apparatus 1' it is possible not only to register the object 2, 3 itself but also, by using a time and temperature recognition unit 17, to register the time and the temperature at which the object was recognized. In this way, a complete movement sequence of an object can be understood. However, the apparatus 1' can also be used to detect a stationary object 2, 3.

Because a line on the wall 6 is scanned in the apparatus 1', the size of the object registered can be determined by using the intensity changes determined per scanned point.

The scanning frequency needed for the application is given by the distance of the laser from the object 2, 3 to be measured and its size. Here, it is necessary that the scanning frequency is chosen in such a way that the distance covered during a cycle, which comprises one pulse period and one pause, is less than half of the object size. For the purpose of measurement of objects, the scanning frequency must be chosen in such a way that the distance covered during a cycle is less than half the required measurement accuracy.

The invention claimed is:

1. An apparatus for recognizing objects with a light source and a light receiver wherein the light source is a laser light source, the apparatus has an at least partly reflective wall and, between the laser light source and the wall, an interspace is provided, through which an object is moved or in which an object is placed, and a movable mirror device is arranged in the beam path between the laser light source and the wall in such a way that light emitted by the laser light source is directed onto the wall, wherein the movement of the mirror device is controlled in such a way that the wall can be irradiated with the light emitted by the laser light source, at least along a line, and light reflected from the wall is detected by the light receiver, characterized in that the wall is curved, further characterized in that the object is a ball, which is held on a softenable layer in a ring holder, below which a measurement region for registering the ball is provided at a distance of 25.0+0.4 mm.

2. The apparatus according to claim 1, characterized in that the object is arranged in a transparent vessel such that it can fall downward and the wall is provided curved on one side of the vessel.

3. The apparatus according to claim 2, characterized in that the vessel is a beaker, which is filled with a transparent liquid, the object being arranged in the liquid.

4. The apparatus according to claim 1, characterized in that the wall has alternating light and dark regions.

5. The apparatus according to claim 4, characterized in that the light and dark regions of the wall form a regular stripe pattern.

6. The apparatus according to claim 5, characterized in that the stripe pattern is a vertical stripe pattern.

7. The apparatus according to claim 1, characterized in that the light emitted by the laser light source is pulsed.

8. The apparatus according to claim 1, characterized in that the mirror device has an electronically controllable oscillating mirror.

9. The apparatus according to claim 1, characterized in that the light receiver has a light sensor which is coupled with an evaluation unit.

10. The apparatus according to claim 9, characterized in that the evaluation unit has a contrast control unit.

11. The apparatus according to claim 1, characterized in that the laser light source and the light receiver are combined in a scanning module having an uncoded high-low output signal.

12. The apparatus according to claim 1, characterized in that the apparatus has a time and/or temperature registering unit.

13. A method for recognizing objects with a light source and a light receiver wherein the light source is a laser light source, from which light is directed onto a movable mirror device, wherein the mirror device directs the light onto a curved, at least partly reflective wall and the mirror device is controlled in such a way that the wall is irradiated by the light, at least along a line, and wherein the light receiver detects the light reflected from the wall and, in the process, registers an object moving or placed between the laser light source and the wall by means of a change in the reflected light detected, characterized in that the object is a ball which, before falling, rests on a layer in a ring arrangement, the layer being softened at a specific temperature and the ball encased by the layer material falling downward, the ball being registered after a specific fall travel.

14. The method according to claim 13, characterized in that an object falling in a transparent vessel is registered, the wall being provided curved on one side of the vessel.

15. The method according to claim 14, characterized in that the vessel is a beaker, which is filled with a transparent liquid, the object being arranged in the liquid.

16. The method according to claim 13, characterized in that the light receiver is connected to an evaluation unit, which outputs a high level for light regions of the wall and a low level for dark regions of the wall in an output signal.

17. The method according to claim 16, characterized in that a regular stripe pattern provided on the wall is registered by the light receiver with the evaluation unit as a continuous, uncoded 0-1 bit pattern.

18. The method according to claim 16, characterized in that the output signal is disturbed by the object in such a way that, in the region in which the object is moved or placed, low levels are registered instead of high levels.

19. The method according to claim 13, characterized in that the light from the laser light source is radiated onto the mirror device in pulsed form.

* * * * *